US008252310B2

(12) United States Patent
Ambühl et al.

(10) Patent No.: US 8,252,310 B2
(45) Date of Patent: Aug. 28, 2012

(54) MANUFACTURE PROCESS

(75) Inventors: Michael Ambühl, Rheinfelden (CH); Corine Gessier-Vial, Altkirch (FR); Christa Hartmann, Basel (CH); Daniel Kaufmann, Bättwil (CH); Ernst Küsters, Eschbach (DE); Ulrich Meier, Riehen (CH); Andreas Meyer, Neuenburg (DE); Nabila Sekkat, Basel (CH)

(73) Assignee: Novartis AG, Basel (CH)

( * ) Notice: Subject to any disclaimer, the term of this patent is extended or adjusted under 35 U.S.C. 154(b) by 882 days.

(21) Appl. No.: 12/001,132

(22) Filed: Dec. 10, 2007

(65) Prior Publication Data

US 2008/0145410 A1    Jun. 19, 2008

(30) Foreign Application Priority Data

Dec. 14, 2006 (EP) .................................. 06126101
Dec. 14, 2006 (EP) .................................. 06126122

(51) Int. Cl.
*A61K 33/26* (2006.01)

(52) U.S. Cl. ....................................................... 424/439

(58) Field of Classification Search ........................ None
See application file for complete search history.

(56) References Cited

U.S. PATENT DOCUMENTS

| | | | | |
|---|---|---|---|---|
| 2,885,393 | A | 5/1959 | Herb | |
| 3,697,502 | A | 10/1972 | Christensen | 260/209 |
| 3,951,821 | A * | 4/1976 | Davidson | 252/1 |
| 4,180,567 | A | 12/1979 | Herb | 424/180 |
| 4,569,836 | A | 2/1986 | Gordon | 424/1.1 |
| 4,599,405 | A | 7/1986 | Muller et al. | 536/113 |
| 4,827,945 | A | 5/1989 | Groman | 128/653 |
| 4,828,813 | A | 5/1989 | Pich et al. | 424/480 |
| 4,927,756 | A | 5/1990 | Schwengers | 435/103 |
| 4,970,079 | A | 11/1990 | Hem et al. | 424/646 |
| 5,043,101 | A | 8/1991 | Gordon | 752/408 |
| 5,055,288 | A | 10/1991 | Lewis et al. | 424/9 |
| 5,234,697 | A | 8/1993 | Sipos | 424/400 |
| 5,492,814 | A | 2/1996 | Weissleder | 435/725 |
| 5,514,281 | A | 5/1996 | Boos | 210/645 |
| 6,174,442 | B1 | 1/2001 | Geisser et al. | |
| 2004/0186073 | A1 | 9/2004 | Seidel et al. | |
| 2005/0107253 | A1 | 5/2005 | Sano et al. | 502/401 |
| 2009/0169645 | A1* | 7/2009 | Muller et al. | 424/646 |

FOREIGN PATENT DOCUMENTS

| | | |
|---|---|---|
| CA | 2 240 668 | 6/1997 |
| CA | 2571364 | 1/2006 |
| DE | 10 2004 03118 | 1/2006 |
| EP | 0600347 | 6/1994 |
| EP | 0 585 898 | 8/1998 |
| EP | 1457256 | 9/2004 |
| WO | 92/01458 | 2/1992 |
| WO | 97/22266 | 6/1997 |
| WO | 99/15189 | 4/1999 |
| WO | 2006/000547 | 1/2006 |

OTHER PUBLICATIONS www.niro.com/fluidized-spray-dryer.html, published online on Feb. 1, 2001, retrieved on Oct. 28, 2010.*
Budavari S. et al., The Merck Index, 11th edition, Merck & Co., p. 632, (1989).
Eybl et al., "Interaction of Chelating Agents, Ferric Dextran and Zinc with indium in mice", Acta Pharmacologica et Toxicologica, vol. 59, pp. 475-477, (1986).
Choy, D. et al., "The effective of iron-dextran on the biodistribution of technetium pyrophosphae", International Journal of Nuclear Medicine and Biology, vol. 9, pp. 277-282, (1982).
Heldenberg et al., "Effect of iron on serum 2.5-hydroxyvitamin D and 24, 25-dihydrovitamin D concentrations", The American Journal of Clinical Nutrition, vol. 56, No. 3, pp. 533-536, (1992).
Boudinot et al., "Fluid shifts and other factors affecting plasma protein binding of prednisolone by Equilibrium dialysis", Journal of Pharmaceutical Sciences, vol. 73, No. 6, pp. 774-780, (1984).
Nova et al., "Dialyzable Drugs", American Journal of Nursing, vol. 87, No. 7, pp. 933-942, (1987).
Burt, H et al., "Ion-Exchange resins as Potential Phosphate-Binding Agents for Renal Failure Patients Effects of the Physicochemical Properties of resins on Phosphate and bile Salt Binding", Journal of Pharmaceutical Sources, vol. 76, No. 5, pp. (1987).
Hercz, G. et al., "Prevention of Phosphate Retention and Hyperphosphatemia in Uremia", Kidney International, vol. 32, Suppl. 22, pp. S-215-S-220, (1987).
Jones, W.H. et al., "Quantification of the Binding Tendencies of Cholestyramine III: Rates of Adsorption of Conjugated Bile Salt Anions onto Cholestyramine as a Function of added Inorganic Electrolyte Concentration, Temperature, and Agiration Intensity", Journal of Pharmaceutical Sciences. vol. 59. No. 6. (1970).
Database WPI, Section CH, Week 8522, Derwent Publications, Ltd. (Updated).
Hjerten, S et al., "High-performance absorption chromatography of proteins on deformed non-porous agarose beads coated with insoluble metal compounds", Journal of Chromatography, vol. 481, pp. 175-186, (1989).
Hjerten, S. et al., "High-performance absorption chromatography of proteins on deformed non-porous agarose beads coated with insoluble metal compounds II", Journal of Chromatography, vol. 481, pp. 187-199, (1989).
Muller A., Arzneimittel-Forschung, "Macromolecular Iron (III)-Hydroxid Complexes", vol. 17, No. 8, pp. 921-931, (1967).
Hugo et al, Hugo and Russell's Pharmaceutical Microbiology, 7th Ed., Blackwell Sciences, Ltd., Malden, Massachusetts, USA, p. 294, 2004.

* cited by examiner

*Primary Examiner* — Tracy Vivlemore
*Assistant Examiner* — Jennifer Berrios
(74) *Attorney, Agent, or Firm* — Leslie Fischer (57) ABSTRACT

The present invention relates to a new iron containing phosphate adsorbent and its use e.g. for treating hyperphosphataemia.

9 Claims, 1 Drawing Sheet

Fig 1: Light Microscopy

The bar below represents 500 micrometers.

Fig 2: Scanning Electron Microscopy (SEM) +Energy Dispersive X-ray Analysis (EDX)

The parts in grey correspond to the particles of iron oxide hydroxides; the parts in black represent the starch particles.
The bar below represents 60 micrometer.

MANUFACTURE PROCESS

The present invention relates to new iron containing phosphate adsorbent, process for its production, uses thereof and pharmaceutical compositions containing it.

BACKGROUND OF THE INVENTION

Phosphorus is critical for bone mineralization, cellular structure, genetic coding, and energy metabolism. Many organic and inorganic forms exist. Phosphorus is present in nearly all foods, and GI absorption of dietary forms is very efficient. Phosphorus homeostasis normally is maintained through several mechanisms (renal excretion, cellular release, hormonal control, etc). When the phosphorus load (from GI absorption, exogenous administration, or cellular release) exceeds renal excretion and tissue uptake, hyperphosphatemia occurs.

Hyperphosphatemia is associated with significant increase in morbidity and mortality, and may induce severe complications, such as hypocalcemia, decreasing of vitamin D production, metastatic calcification. Hyperphosphatemia is also contributing to the increased incidence of cardiovascular disease among dialysis-dependent patients, and can result in bone pathology.

At least 70% of patients with renal insufficiency or renal failure show hyperphosphatemia. In many cases, restricting intake of dietary phosphorus is not sufficient to reduce serum phosphate levels into the normal range, and oral phosphate binders need to be taken.

Calcium and aluminium salts orally taken as treatment for hyperphosphatemia are known. But there are concerns regarding their long-term safety. The traditional aluminium-based phosphate binders have the drawback of side effects due to aluminium absorption (osteomalacia, encephalopathy, microcytic anaemia). Calcium-containing phosphate binders (calcium carbonate or calcium acetate) may aggravate metastatic calcification, particularly if they are taken together with vitamin D analogues and a high calcium dialysate concentration.

An iron-based ferric citrate phosphate binder, known as Zerenex™, is described in U.S. Pat. No. 6,903,235B. Zerenex™ is an oral, inorganic, iron-based compound that has the capacity to bind phosphorous and form non-adsorbable complexes. Since this product is soluble its long term administration may induce an increase of the concentration of iron in gastrointestinal tract, which may be safety issue as mentioned hereinabove.

Sevelamer, a synthetic polymer commercialized by Genzyme under the name of Renagel®, poly(allylamine-co-N,N'-diallyl-1,3-diamino-2-hydroxypropane) hydrochloride is an iron exchange gel matrix.

The phosphate binding capacity of metal oxide hydroxides is known in the art. The possible medical application of metal hydroxides and metal oxide hydroxides as phosphate binders is also described. For example WO9201458 discloses a method of controlling serum phosphate level in patients by iron oxy-hydroxides which bind to ingested phosphate.

For example, U.S. Pat. No. 6,174,442, the content thereof being enclosed herewith by reference, describes an adsorbent for phosphate which contains polynuclear β-iron hydroxide stabilized by carbohydrates and/or humic acid. WO 2006/000547, the content thereof being also enclosed herewith by reference, describes an adsorbent for phosphate which is obtained from iron(III) nitrate or sulfate and is stabilized by starch and sucrose.

The phosphate binding capacity of the known phosphate adsorbents containing oxide hydroxides is limited. Furthermore, the processes described to manufacture such compounds are not suitable for preparing larger amounts of compounds.

The possible release of iron under physiological conditions from any iron containing drugs or compounds, in particular in case of the phosphate adsorbent described in U.S. Pat. No. 6,174,442, may be a safety issue, since excess iron is toxic to body organs. Preferably the daily release of iron should not be higher than 20 mg iron per day. A too high release of iron can particularly problematic in case of patients suffering from haemochromatosis. Haemochromatosis is a very common genetic disorder of iron metabolism wherein absorption of iron through the intestine is uncontrolled even when body saturation levels have been reached.

Furthermore the available phosphate binders and the phosphate adsorbents described in the prior art bind not more than about 120 mg phosphate per gram of product. Because of the relatively low adsorption capacity of these phosphate adsorbents, the amount of adsorbent, e.g. the amount and/or number of oral dosage forms containing it to be taken every day must be high. For example the average daily dosage to be taken by dialysis patients in order to avoid/treat hyperphosphatemia is of about 9 capsules in case of Zerenex™, and of 14 film coated tablets in case of Renagel®. This indicates that the patient compliance of the available phosphate adsorbents is very low.

Due to the high levels of phosphate contained in diet and the relatively low adsorption capacity of the phosphate adsorbents available or described in the prior art, it is necessary to administer such adsorbents in high dose in order to efficiently control the blood level of phosphate. Therefore even a small increase in phosphate binding capacity may permit to decrease the dose of adsorbent to be administered every day, for example to lower the number of oral dosage forms to be administered every day. So even a small increase in phosphate binding capacity would be beneficial to the patient, e.g. would improve patient compliance.

Therefore there is a need to provide a phosphate adsorbent with a high phosphate binding capacity to be usable as a pharmaceutical.

Furthermore there is a need to provide a manufacture process which lead to an adsorbent which is homogenous and stable, and which can be easily formulated and/or packaged, and which can be performed on a large scaling without affecting the properties of the adsorbent, i.e. its phosphate binding capacity.

SUMMARY

The present invention provides a new phosphate adsorbent containing iron(III) oxide-hydroxide having higher phosphate binding capacity than the phosphate adsorbent available yet, or than the iron(III)-based phosphate adsorbent described in the prior art, as well as uses thereof and pharmaceutical compositions containing it. In particular the present invention pertains to a polynuclear iron(III)-based phosphate adsorbent comprising i) an adsorbent base material, preferably a non soluble carbohydrate, ii) polynuclear iron(III) oxide hydroxides, and iii) a soluble carbohydrate, wherein the soluble carbohydrate is incorporated, e.g. partially incorporated, into the polynuclear iron(III) oxide hydroxides. The polynuclear iron oxide hydroxides may be stabilized by soluble carbohydrates. The iron(III)-based phosphate adsorbent may further comprise a carbonate; the carbonate may partially incorporated, e.g. partially incorporated, into the polynuclear iron(III) oxide hydroxides.

The present invention further provides an iron(III)-based phosphate adsorbent containing polynuclear iron(III) oxide hydroxides wherein the polynuclear iron oxide hydroxide contains polynuclear gamma-iron oxide hydroxides, and optionally ferrihydrite, e.g. traces of ferrihydrite. The polynuclear iron oxide hydroxide may be stabilized by soluble carbohydrates.

It is believed that the iron(III)-based phosphate adsorbent according to the present invention is a complex formed with polynuclear iron(III) oxide hydroxides, insoluble carbohydrate such as starch, and soluble carbohydrate such glucose derivative (e.g. sucrose or maltodextrin). The iron oxide-hydroxide contained in the iron(III)-based phosphate adsorbent according to the present invention would then be a complex, as a whole insoluble under the physiological conditions, which is stabilized by the glucose derivative. The glucose derivative is probably acting by preventing the phosphate adsorbent from being overdried during its purification, as overdrying would lead to a loss of the phosphate binding capacity.

The present invention further provides a manufacture process for producing an iron(III) based phosphate adsorbent. In particular there is provided a process for manufacturing and isolating the iron(III) based phosphate adsorbent in a form which is easily packaged, e.g. as a dry powder suitable for direct sachet filling.

Furthermore the present invention provides a manufacture process for preparing oxide-hydroxide of iron having gamma-configuration from iron (III), i.e. a manufacture process for preparing oxide-hydroxide of iron(III) having gamma-configuration.

DESCRIPTION

Iron(III)-Based Phosphate Adsorbent

Figure 1:
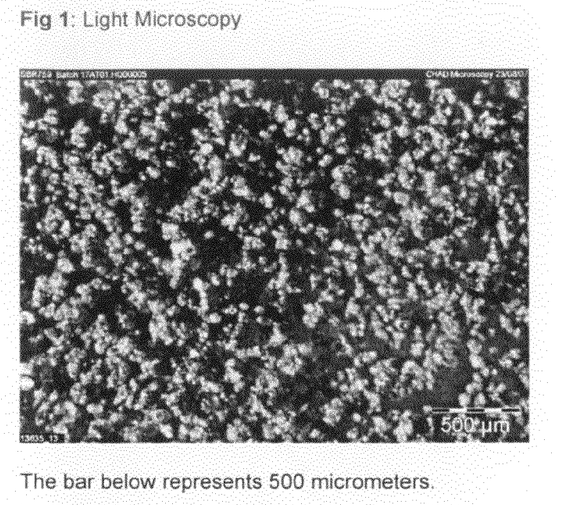
FIG. 1: Light Microscopy of the iron(III)-based phosphate adsorbent according to one embodiment of the present invention
Figure 2:
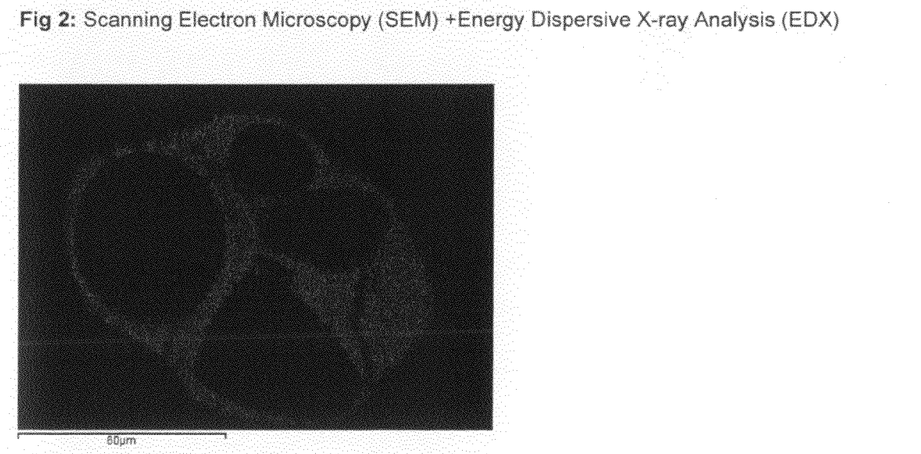
FIG. 2: Scanning Electron Microscopy (SEM) plus Energy Dispersive X-ray Analysis (EDX) (block phase analysis) of the iron(III)-based phosphate adsorbent according to one embodiment of the present invention. It represents a more detailed picture of one of the particles shown in FIG. 1.

Surprisingly it has been found that by using dedicated reaction conditions during the manufacture process of a polynuclear iron it is possible to prepare a polynuclear iron(III)-based phosphate adsorbent which has a higher phosphate binding capacity than the phosphate adsorbents of the prior art, in particular than the iron-based phosphate adsorbents described in the prior art.

Furthermore, in order to obtain an iron oxide-hydroxide containing compound having a good phosphate binding capacity which can be used as a pharmaceutical, it is necessary to have an iron-based compound which is stable. It is known that iron oxide-hydroxides, in particular iron(III) oxide-hydroxides, are not stable compounds: during time ageing occurs which leads to the re-grouping of initially randomly placed molecules and to the formation of a more or less regular crystal lattice. Ageing usually not only involves crystallization but also particle enlargement. Such ageing may alter the phosphate binding of an iron oxide-hydroxide based phosphate adsorbent.

Such an ageing may also lead to an iron-based phosphate adsorbent which does release iron. The possible release of iron from an iron-containing drug could be a safety concern since an excess of iron is toxic to body organs. Therefore there is a need to provide an iron(III)-based phosphate adsorbent which does not release iron, or does release only small amounts of iron under physiological conditions, e.g. an iron amount smaller than the daily acceptable dosage of 20 mg iron. This means that there is a need to provide an iron(III)-based phosphate adsorbent which has a low bioavailability, preferably which is not bioavalaible at all.

Therefore it is necessary to avoid the undesired transformation into iron-oxides which would have a lower phosphate binding capacity and/or a higher iron bioavailability. Surprisingly, it has been found that it is possible to prevent ageing of the iron oxide-hydroxide by using dedicated reaction conditions and auxiliary materials like soluble and soluble carbohydrates, e.g. starch and sucrose.

According to the invention there is provided a new iron-based phosphate adsorbent for the adsorption of phosphate, which has higher phosphate binding capacity than the phosphate adsorbents of the prior art, as herein defined as "phosphate adsorbent of the invention" or "compound of the invention".

Higher phosphate binding capacity means about 15% higher than the phosphate adsorbents known in the art, e.g. at least 20% higher, e.g. at least 25% higher, e.g. at least 30% higher e.g. than the adsorbent described in U.S. Pat. No. 6,174,442. For example, the compound of the invention may adsorb more than about 12% m/m phosphate, preferably more than about 14% m/m, even more preferably about or more than about 20% m/m. As herein defined, % m/m refers to percentage of mass to mass, i.e. to the amount of phosphate (calculated as $PO_4^{3-}$) being adsorbed (in g) by 1 g of phosphate adsorbent.

According to the invention, there is provided an iron-based phosphate adsorbent comprising i) an adsorbent base material, preferably a non soluble carbohydrate, ii) polynuclear iron (III) oxide hydroxides, and iii) a soluble carbohydrate, wherein the soluble carbohydrate is partially incorporated into the polynuclear iron(III) oxide hydroxides. As herein defined "partially incorporated" means that about 10 to 20% by weight of the soluble carbohydrate, based on the total weight of the phosphate adsober, are incorporated into the polynuclear iron (III) oxide hydroxides, i.e. can not be removed by washing the phosphate adsober.

As herein defined, "adsorbent base material" refers to a porous material, preferably having organic or inorganic OH groups, e.g. non soluble carbohydrates; organic polymer or copolymer; natural semisynthetic or synthetic linear and/or branch-chained; soluble or insoluble polyhydroxyl compounds (e.g. polyvinyl alcohol); inorganic supports, e.g. based on silicon dioxide and/or silicates such as glyceryl-modified glasses. Preferred adsorbent base materials are non soluble carbohydrates.

Examples of non soluble carbohydrates include starch, agarose, dextran, dextrin, cellulose. Preferred non soluble carbohydrate is starch.

According to the present invention, "soluble carbohydrate" refers to glucose derivatives, such as sucrose, maltodextrin or mixture thereof. Preferred soluble carbohydrate is sucrose.

Preferably the iron-based phosphate adsorbent of the invention is a iron(III) oxide-hydroxide containing compound, comprising a soluble carbohydrate such as a glucose derivative (e.g. sucrose or maltodextrin), and starch.

In one embodiment of the invention, the phosphate adsorbent may be defined as a complex formed with polynuclear iron(III) oxide hydroxides, starch and the glucose derivative (e.g. sucrose or maltodextrin, preferably sucrose). In a preferred embodiment, the polynuclear iron oxide hydroxides is bound to the adsorbent base material, e.g. starch.

In one embodiment of the invention, the compound of the invention comprises starch particles covered by iron(III) oxide-hydroxide and optionally stabilized by a glucose derivative such as sucrose, maltodextrin or mixture thereof. Preferably the iron is homogenously distributed on the surface of the particles.

In yet a further aspect of the invention there is provided a new iron-based phosphate adsorbent which releases little iron in simulated gastric fluids (as defined in Pharmacopeia). For example, the phosphate adsorbent of the invention does not significantly release iron at a pH range above 2 up to 10. In one example, 10 g of the phosphate adsorbent of the invention may release less than about 20 mg of iron at pH's above 2.

In yet a further aspect of the invention the compound of the invention may contain about 10 to about 35 wt %, e.g. about 20 to about 30 wt %, preferably at least about 20 weight % of non soluble carbohydrate, e.g. starch, for example about 10 to 30, e.g. about 30, e.g. about 28 weight % of starch, based on the total weight of the compound.

In yet a further aspect of the invention there is provided a new phosphate adsorbent containing iron (III) oxide-hydroxide and starch, which contains about 5 to about 50 weight % of soluble carbohydrate, e.g. about 10 to about 40 weight %, e.g. about 12 to about 30 weight %, based on the total weight of the adsorbent. For example, the adsober of the invention contains at least about 10 weight % of sucrose, maltodextrin or mixture thereof (preferably sucrose), for example at least about 14 weight % of sucrose, maltodextrin or mixture thereof (preferably sucrose), for example about 28 wt % of sucrose, maltodextrin or mixture thereof (preferably sucrose), based on the total weight of the compound.

In yet a further aspect of the invention there is provided a new phosphate adsorbent containing iron(II) oxide-hydroxide, which contains more than about 5 weight % of water, for example about 5 to about 10 weight %, for example about 5 to about 8 weight %, based on the total weight of the compound.

In yet a further aspect of the invention the phosphate adsorbent of the invention contains at least about 10 weight % of iron, for example at least about 18 weight %, for example about 30 weight % of iron, e.g. iron(III), based on the total weight of the adsorbent. In another aspect of the invention the iron content of the compound of the invention is about 10 to about 35 weight %, for example about 15 to about 30 weight %, for example about 25 to about 30 weight %, based on the total weight of the compound.

In yet another aspect of the invention there is provided a new iron(III)-based phosphate adsorbent comprising starch and a glucose derivative such as sucrose, maltodextrin or mixture thereof (preferably sucrose), which contains about 5 to about 10 weight % of water, about 20 to about 30 weight % of iron, based on the total weight of the adsorbent.

Preferably the phosphate adsorbent of the invention comprises iron(III), more preferably γ-iron(III) oxide-hydroxide, optionally mixed to ferrihydrite. In a preferred embodiment, the polynuclear iron oxide hydroxide of the phosphate adsorbent consists of gamma-iron oxide hydroxide (preferably gamma-iron(III) oxide hydroxide) or mixture of gamma-iron oxide hydroxide with ferrihydrite.

In another embodiment of the invention, the compound of the invention is x-ray amorphous.

The phosphate adsorbent of the invention is obtained by reacting an aqueous solution of an iron salt, preferably an iron(III) salt, with an aqueous base wherein the precipitation of the salt is performed in presence of an insoluble carbohydrate, preferably starch. The resulting iron oxide hydroxide is stabilized by adding a soluble carbohydrate to the precipitate before the iron hydroxide ages.

Gamma-Iron (III) Manufacture Process

It was not expected that it is possible to selectively obtain gamma-iron(III) (γ-iron (III)) oxide-hydroxide, as well as mixtures of γ-iron (III) oxide-hydroxide with ferrihydrite, directly from an iron(III) source (such as iron (III) chloride) without having to use iron(III) and a subsequent oxidation step.

The present invention also includes a new process for the preparation of gamma-iron(III) oxide-hydroxide, which process comprises the steps of reacting an aqueous solution of an iron (III) salt with an aqueous base, at pH comprised between 6 and 10, optionally in presence of starch. Starch may be added after the reaction of step a), i.e. after the after the complete mixing of the iron salt with the base.

If not present in step a), starch may be added in a further step (step b), e.g. after the complete mixing of the iron salt with the base. In another embodiment, starch is added in step a) and more starch is added in step b).

In both embodiments, the precipitation of the salt by the base is done in presence of starch.

Optionally the obtained precipitate is isolated and washed, as hereinbelow defined.

In another embodiment of the reaction, the aqueous base may consist of an aqueous basic mixture of a base and starch. The reaction may be performed at ambient temperature, or preferably at low temperature.

The iron salt may be iron(III) chloride, iron(III) nitrate or iron(III) sulfate, preferably the iron salt is iron chloride.

The iron(III) oxide-hydroxide obtained by that process has gamma configuration. Small amounts of ferrihydrite, e.g. traces thereof, may also be present.

Iron(III)-Based Phosphate Adsorbent Manufacture Process.

Surprisingly, it has been found that it is possible to obtain iron oxide-hydroxide containing phosphate adsorbent in an excellent quality, i.e. homogenous and stable, by having carbohydrates, e.g. starch and/or sucrose, present during the reaction of the iron with the base and/or by carefully controlling the pH of that reaction. The presence of the carbohydrates prevent the ageing of the iron oxide-hydroxide, i.e. the conversion of the initially formed iron oxide-hydroxide to a less potent phosphate binder. Unexpectedly it has been found that by carefully controlling the pH of reaction, a product with an unexpected high phosphate binding capacity can be synthesized.

The preparation of iron oxide-hydroxides is known in the prior art and is described in U. Schwertmann and M. R. Cornell "Iron oxides in the Laboratory", Wiley-VCH, Second, completed revised and extended edition, 1991. This document teaches that it is possible to prepare β-iron (III) hydroxide. i.e. to obtain iron(III) hydroxide with the β-configuration (beta-configuration) from iron(III), and to prepare gamma-iron (II) oxide-hydroxide, i.e. to obtain iron oxide-hydroxide having gamma-configuration (i.e. γ-configuration) from iron (II).

It is known that even minor changes in the reaction conditions used to prepare the iron oxide-hydroxide, such as pH, ratio of the base to the iron, iron concentration, etc, may prevent the desired product from being obtained (see page 65 of U. Schwertmann and M. R. Cornell). In particular simply scaling the quantities up or down to produce different amounts, in particular higher amounts, of iron oxide-hydroxide may result in the production of a product having a different structure.

In order to obtain an iron-base compound which can be used as a pharmaceutical, it is necessary to have a manufacture process leading to a product always showing a high phosphate binding capacity, e.g. always having the same structure. This need must particularly be fulfilled in case of large scaling up. Surprisingly, it has been found that it is possible to prepare large amounts of an homogeneous iron (III) based phosphate adsorbent, e.g. several grams thereof, by using adequate reaction conditions, i.e., by using a stabilizer during the thermal stress, such as sucrose, and/or by isolating the product by a mild method such as spray drying or fluidized spray drying.

The present invention also includes a process for the preparation of a iron(III)-based phosphate adsorbent comprising iron(III) oxide-hydroxide, insoluble carbohydrate (e.g. starch) and a soluble carbohydrate (e.g. glucose derivative), which process comprises the steps of
i) reacting, e.g. simultaneously mixing, an aqueous solution of iron(III) salt with an aqueous base at pH between 6 and 10, e.g. between 6 and 8, between 6.5 and 7.5, preferably around 7,
either performing step i) in presence of an insoluble carbohydrate, e.g. starch, and optionally adding more insoluble carbohydrate after the complete mixing:
or adding the insoluble carbohydrate after the reaction of step i), e.g. after the complete mixing, wherein in both cases the insoluble carbohydrate is added before completion of the salt precipitation;
ii) isolating the precipitate formed, and optionally washing, e.g. with water;
iii) suspending the precipitate, e.g. in water; and
iv) adding a soluble carbohydrate; and optionally
v) adding at least one excipient selected from a preservative and a binder.

In step i) the aqueous solution of iron(III) salt with the aqueous base leads first to nucleation and then to precipitation of the iron oxide hydroxide. The nucleation may be performed in presence of the insoluble carbohydrate, e.g. starch, or the carbohydrate may be added after the nucleation, and before the precipitation. According to the invention, the precipitation of the salt is performed in presence of the insoluble carbohydrate, preferably starch. The insoluble carbohydrate may be added before the precipitation occurs, or during the precipitation. Preferably the insoluble carbohydrate is added before the precipitation is complete.

Preferably, the aqueous solution of iron(III) salt is mixed to the aqueous base in presence of the insoluble carbohydrate, e.g. starch. Optionally additional insoluble carbohydrate is then added. In another embodiment of the invention, the insoluble carbohydrate is added only after having mixed the aqueous base with the iron salt, for example after the precipitation of the iron salt has started.

It is believed that the insoluble carbohydrate may stabilize the precipitate. Unexpectedly, it has been found that performing the precipitation in presence of an insoluble carbohydrate increases the phosphate binding capacity of the iron(III)-based compound thus obtained, preferably starch. The resulting iron oxide hydroxide may be stabilized by adding a soluble carbohydrate to the precipitate before the iron hydroxide ages.

The iron(III) salt may be iron(III) chloride, iron(III) nitrate or iron(III) sulfate, preferably the iron salt is iron(III) chloride, e.g. solid iron(III) chloride hexahydrate. The aqueous solution of iron(III) salt may be in particular a solution of iron(III) salt, as herein above defined, in water. The solution of iron salt may comprise from about 3 to about 35 wt/wt %, e.g. 20 to about 30 wt/wt % of iron salt, preferably about 25 wt/wt % of iron salt, based on the total weight of the iron salt. Preferably, a solution of iron(III) chloride at about 20 to 30 wt/wt %, preferably about 25 wt/wt %, based on the total weight of the iron salt, is used.

According to the invention, it is also possible to use other aqueous iron solution, such as iron alum (e.g. $KFe(SO_4)_2$ or $NH4Fe(SO_4)_2$) or sulfuric-acid-containing solutions or iron (III), e.g. of iron (III) sulfate.

The base to be used may be hydroxide or carbonates of alkali or alkaline earth metals. Alkali carbonates, alkali bicarbonates and alkali metal hydroxides (e.g. of sodium) are preferred. In particular, the base may be selected from LiOH, KOH, NaOH, $Ca(OH)_2$, $Mg(OH)_2$, $Li_2CO_3$, $K_2CO_3$, $CaCO_3$, $MgCO_3$, preferably $Na_2CO_3$. The base solution may comprise about 20 to about 30, e.g. about 22 to about 27, e.g. about 25.5 vol % of base, based on the total volume of the solution.

The aqueous base may consist of an aqueous solution containing a base, as hereinabove defined, and an insoluble carbohydrate, e.g. starch.

The amount of base is chosen in order to obtain the desired pH, e.g. to adjust the pH of the solution resulting from the mixture with the aqueous solution of iron(III) salt to a pH between about 6 and 10, preferably about 6 and 8, more preferably about 6.5 and 7.5, even more preferably around 7.

Starch may be selected from corn, wheat, rice, maize or potato starch, and mixture thereof. Starch may also contain part of soluble starch (e.g. maltodextrin). For example, starch may be a mixture of 80 wt % or more of potato starch and 20 wt % or less of soluble starch, e.g. 80 wt % or more of potato starch and 20 wt % or less of maltodextrin. In another embodiment of the invention, the starch is replaced by a dietary fiber, e.g. Benefiber® (produced by Novartis AG). Preferably starch is potato starch.

Preferably e.g. 1 g of insoluble carbohydrate, e.g. starch, is added per about 0.5 to about 30 g of iron salt, e.g. per about 1.0 to about 20 g of iron salt, e.g. per about 1.5 to about 10 g of iron salt, e.g. per about 2.0 to about 15 g of iron salt.

In a preferred embodiment of the invention, in step i) the pH of the solution is maintained constant at a pH between 6 and 8, preferably around 7, during all the mixing. By simultaneously addition of the iron salt and the base, the pH can be adjusted to the desired value.

According to the invention, the reaction, in particular step i), is preferably made at a temperature between about 1 and 20, preferably 2 to 10, preferably about 5° C. In another embodiment step i) is performed at ambient temperature.

Subsequently to step ii) the suspension may stagnate for a short time, e.g. more than 1 hour, preferably during 1 to 5 hours, more preferably over night. During that time, the suspension can be stirred.

According to the invention, the soluble carbohydrate may be a glucose derivative. Glucose derivatives may be selected from agarose, dextran, dextrin, dextran derivatives, cellulose, cellulose derivatives, sucrose, maltose, lactose, mannitol and mixture thereof. Preferred glucose derivatives are sucrose, maltodextrin and mixture thereof. Most preferred glucose derivative is sucrose.

According to the invention, the amount of soluble carbohydrate, e.g. glucose derivative, added in step iv) may be of about 5 to about 15% wt, preferably about 5 to about 10, based on the weight of the phosphate adsorbent. Preferably about 5 to about 15 weight % sucrose or about 5 to about 10 weight % sucrose is used.

According to the invention, the precipitate obtained in step i) may be washed, at least one time.

According to the invention, in step ii) the obtained precipitate is isolated, e.g. by decantation, filtration, centrifugation, preferably by decantation, and then washed. The washing is performed with water or an aqueous solution of $NaHCO_3$, preferably with water. Combinations of water washings and $NaHCO_3$-washings may be used. The precipitate is washed once or several times, preferably several times. Washing can be done until the level of impurities is down to a predefined level, e.g. from a few hours up to a few days. Preferably 2 to 5 washings are done, more preferably 3 to 5. After each washing operation the water or washing solution is removed by decantation, filtration, centrifugation, preferably by decantation. Preferably, the product is not completely dried.

The product is then resuspended in water. A minimum amount of water is needed so that the suspension can be processable. For example the ratio amount of water/final phosphate adsorbent may be from about 0.8 to about 2, preferably 1.1. to 1.5, more preferably about 1.

The resulting aqueous suspension of phosphate adsorbent has approximately a neutral pH value in the range of about 6.5 to 7.5.

The suspension may also be done in presence of a soluble carbohydrate as herein above defined, e.g. sucrose, e.g. the suspension is performed with an aqueous solution of soluble carbohydrate. Or the soluble carbohydrate is added in a further step, after the precipitate is resuspended.

In step iv), preferred soluble carbohydrate is sucrose.

In step iv), the preservative may be a soluble preservative, such as e.g. chlorhexidien or p-hydroxy-benzoic acid ester, or an alcohol, such as e.g. ethanol, methanol, 2-propanol or combination thereof. Preferably, the preservative is an alcohol. Preferred alcohol is ethanol.

In one embodiment of the invention, the phosphate adsorbent resulting from step v) is not dried, e.g. not completely dried.

Optionally a further step (i.e. step vi) can be added which consists of isolating the phosphate adsorbent. Such an isolation may be made by filtration, decantation, spray drying or fluidized spray drying. Preferably spray drying or fluidized spray drying, e.g. fluidized bed spray drying is performed. Unexpectedly, it was found that such a technique leads to produce a well granulated, free flowing and dust free powder which is suitable for direct sachet filling, without the use of excipients. That powder can easily be manipulated, e.g. during processing or packaging.

According to the invention, there is provided a process for manufacturing an iron(III)-based adsorbent having high phosphate binding capacity in form of a dry powder, as hereinabove described, wherein the process further comprises a step of isolating the product by spray drying or fluidized spray drying.

Surprisingly, it has been found that fluidized bed spray drying is suitable to directly and continuously produce a well granulated, free flowing and dust free powder which is suitable for direct sachet filling or can be easily granulated to yield a granulate.

In another preferred embodiment of the invention, the surface area of the iron(III)-based phosphate adsorbent is increased, e.g. by adding a porous excipient, e.g. silicon dioxides, for example Aerosil, during the manufacture of the phosphate adsorbent, e.g. during step vi) as herein above described.

Furthermore a formulation step may be performed. For example a step of mixing, granulating, encapsulating and/or tabletting the phosphate adsorbent may be done, with adequate excipients if necessary.

In one embodiment of the invention, the process further comprises the step vii) of granulating the powder, optionally in presence of at least one excipient selected from a binder and a lubricant, to yield an iron(III)-based phosphate adsorbent as a granulate In another embodiment of the invention, the process further comprises the step viii) of tabletting the product, i.e. tabletting either the powder obtained in step vi) or the granulate obtained in step vii). The tabletting step is optionally performed in presence of an excipient selected from a filler, a binder, a disintegrant, a flow agent, a lubricant, and mixture thereof.

Formulation

It is known that iron oxides are difficult to be manufactured because of their dustiness. Such a dustiness may also be problematic for formulating iron oxides containing compounds in form of pharmaceutical compositions and/or for packaging such compounds. In particular, if iron oxides are to be taken as powder, fine dust can be whirled by air or can even be inhaled, which may lead to losing part of the iron oxides, or taking an incorrect dosage thereof. Therefore it is important to prepare a pharmaceutical composition containing an iron(III)-based phosphate adsorbent which can be safety administered to the patients, in particular whose dosage can be controlled when taken by the patients.

In order to obtain an iron oxides containing phosphate adsorbent efficiently suitable as pharmaceutical which can be orally administered, it is necessary to obtain a compound which can be formulated into oral pharmaceutical compositions. Typical oral formulation contain excipients present to facilitate automatic compaction or sachet filling. However addition of such excipients may affect the phosphate binding capacity of the adsorbent. Therefore in a preferred embodiment of the invention, the phosphate adsorbent is in form of a powder. Surprisingly it has now been found that by using dedicated processing conditions during the manufacture process, addition of such excipients may be avoided.

Due to the daily amount of phosphate eaten every day through food intake and the relative low binding phosphate capacity of the phosphate adsorbents, patients who need to take such compounds, e.g. suffering from hyperphosphateamia, need to take high amount of them every day. Therefore there is a need to provide a phosphate adsorbents in a formulation which could improve patience compliance, for example in case of elderly or pediatric patients. A formulation in form of a powder could improve patience compliance in comparison to the phosphate adsorbents commercially available, since the powder could be diluted in water and then permit to take higher doses of phosphate adsorbent with a low amount of liquid.

Surprisingly the inventors of the present invention were able to prepare an iron oxides containing phosphate adsorbent in form of a non-dusty and free-flowing powder without the use of excipients while maintaining the high phosphate binding capacity of the compound. That powder can easily be manipulated, e.g. during processing or packaging. For example that powder can be easily filled, e.g. mechanically filled, into sachets or stick packs.

The present invention provides a phosphate adsorbent which is free-flowing, almost dust-free and then can be filled into sachets or stick packs, e.g. automatically filled.

According to the present invention, pharmaceutical composition of the invention refers to pharmaceutical composition containing iron (III)-based phosphate adsorbent, e.g. the containing the phosphate adsorbent of the invention.

Pharmaceutical compositions according to the invention may be formulated in any conventional form, preferably oral dosage forms, e.g. powders, granules, granulates, capsules, sachets, stick packs, bottles (optionally together with adequate dosing systems, e.g., calibrated spoons), tablets, dispersible tablets, film coated tablets, or uniquely coated tablets Pharmaceutical compositions according to the invention may also be formulated as semi-solid formulations, e.g. aqueous and non aqueous gel, swallowable gel, chewy bar, fast-dispersing dosage, cream ball chewable dosage form, chewable dosage forms, or edible sachet as defined hereinbelow.

Preferred formulations are powder, granulate, tablet, for example dispersible tablet.

In a preferred embodiment of the invention, the pharmaceutical composition is prepared in the form of a powder or a granulated product (i.e. granulated powder or ganulates), which is optionally filled into powder containers such as bottle, capsule, sachet or stick pack. Optionally such a sachet or stick pack is supplied with a child resistant easy opening feature. A lubricant, as defined hereinbelow, may be added, for example in case the phosphate adsorbent of the invention, e.g. as prepared according to the manufacture process defined hereinabove, is filled into a capsule.

The granulated product may be prepared by dry granulation, e.g. roller compaction, or wet granulation, for example in a fluid bed or high shear mixer. The granulation may be done in presence of a binder, e.g. MCC, in order to improve the mechanical stability of the granulate. The granulates may be filled then into e.g. bottles, capsules, sachets or stick packs. In one embodiment of the invention such filling can be performed by automatically working systems.

The sachet or stick packs may contain between about 0.5 to 10 g, e.g. from about 0.5 to 5 g of granulated product.

The pharmaceutical composition of the invention may contain a binder, e.g. dry binder, such as sucrose or microcrystalline cellulose (MCC).

In another embodiment of the invention, the pharmaceutical composition of the invention may contain a lubricant, e.g. Mg-stearate or hydrophilic lubricant, such as PEG 6000 or PEG 4000. The invention provides a capsule containing the iron(III)-based phosphate adsorbent, e.g. as a powder or a granulate, and preferably further comprising a lubricant.

According to one embodiment of the invention, the pharmaceutical composition is in form of a tablet. For better applicability or ease of differentiation, a subsequent film coating of the tablet may be performed.

The tablet may be produced by tabletting, e.g. direct compressing, the phosphate adsorbent as a pure powder, i.e. without containing excipient.

In another embodiment of the invention, the tablet is prepared by compression of the pure powder, i.e. a powder of the phosphate adsorbent without excipient, together with suitable excipients, such as excipients selected from filler, binder, disintegrant, flow agent, lubricant, and mixture thereof.

In yet another embodiment of the invention, the tablet is obtained by compression of the granulated powders (i.e. the "inner phase") together with further excipients (the "outer phase"). The inner phase of the pharmaceutical composition according to the invention may comprise the phosphate adsorbent, and at least one excipient selected from a filler, a binder, a disintegrant, and mixture thereof. The outer phase of the pharmaceutical composition according to the invention may comprise at least one excipient selected from a flow agent, a lubricant, a filler, a disintegrant and mixture thereof.

Preferably the outer phase comprises a flow agent, a lubricant, and optionally a filler and/or disintegrant.

The pharmaceutical compositions according to the present invention may comprise a filler to provide processability.

Suitable filler materials are well-known to the art (see, e.g., Remington's Pharmaceutical Sciences, 18th Ed. (1990), Mack Publishing Co., Easton, Pa., pp. 1635-1636), and include microcrystalline cellulose, lactose and other carbohydrates, starch, pregelatinized starch, e.g., starch 1500R (Colorcon Corp.), corn starch, dicalcium phosphate, potassium bicarbonate, sodium bicarbonate, cellulose, calcium phosphate dibasic anhydrous, sugars, sodium chloride, and mixtures thereof, of which lactose, micro-crystalline cellulose, pregelatinized starch, and mixtures thereof, are preferred. Owing to its superior disintegration and compression properties, microcrystalline cellulose (Avicel grades, FMC Corp.), and mixtures comprising microcrystalline cellulose and one or more additional fillers, e.g., corn starch or pregelatinized starch, are particularly useful. Preferably the filler is microcrystalline cellulose.

The filler may be present in an amount of about 10 to 40 wt. %, based on the total weight of the pharmaceutical composition, preferably 20 to 40 wt %, more preferably about 30 wt %.

The pharmaceutical composition of the invention may contain also the following classes of excipients:

a) well-known tableting binders (e.g., hydroxypropylmethylcellulose, starch, starch pregelatinized (starch 1500) gelatin, sugars, natural and synthetic gums, such as carboxymethyl-cellulose, methylcellulose, polyvinylpyrrolidone, low substituted hydroxypropylcellulose, ethylcellulose, polyvinylacetate, polyacrylates, gelatin, natural and synthetic gums), micro-crystalline cellulose, and mixtures of the foregoing. In a preferred embodiment the binder consists of low substituted hydroxypropylcellulose HPC (e.g. HP cellulose-LH22) or hydroxypropylmethylcellulose HPMC, e.g. 3 or 6 cps.

The tableting binder may be comprised between about 1 and about 10 wt. %, and preferably about 1 and about 5 wt. %, based on the total weight of the pharmaceutical composition. In a preferred embodiment, the binder is used at about 3 wt %, based on the total weight of the pharmaceutical composition.

b) disintegrants, e.g. carboxymethylcellulose, cross-linked sodium carboxymethyl-cellulose (croscarmelose sodium), crospovidone, sodium starch glycolate. Preferred disintegrants are crospovidone and croscarmelose sodium.

The disintegrant may be comprised between about 3 and about 15 wt. %, preferably about 5 and about 10 wt %, based on the total weight of the pharmaceutical composition. For example, the disintegrant is crospovidone, croscarmelose sodium or mixture thereof, and is contained at about 10 wt %, based on the total weight of the pharmaceutical composition.

c) lubricants, e.g. magnesium stearate, stearic acid, calcium stearate, glyceryl behenate, hydrogenated vegetable oil, carnauba wax and the like, polyethylene oxides such as PEG 6000 or PEG 4000. In a preferred embodiment lubricant is magnesium stearate.

The lubricant, e.g. magnesium stearate, may be present from about 0.5 to about 5 wt %, e.g. from about 3 to about 5 wt %, preferably about 2 to about 3%, based on the total weight of the pharmaceutical composition.

d) flow agents, e.g. silicon dioxide or talc, preferrably silicon dioxide colloidal (e.g. Aerosil). The flow agent, e.g. silicon dioxide colloidal, may be present from about at about 0.1-2 wt %, e.g. 0.5 w %, based on the total weight of the pharmaceutical composition.

e) anti-adherents or glidants, e.g., talc;
f) sweeteners;
g) opacifying or coloring mediums, e.g. titanium dioxide, iron oxide or aluminum lakes;
h) flavoring mediums;
i) antioxidants.

According to the invention, there is provided a tablet containing the iron(III)-based phosphate adsorbent, and a lubricant, and optionally at least one further excipient selected from a filler, a binder, a disintegrant, and a flow agent, as hereinabove described. The tablet may further comprise at least one excipient selected from an anti-adherent, a glidant, a sweetener, an opacifying or coloring medium, and a flavoring medium, as hereinabove described.

The tablet may be coated, e.g. may comprise a film coating. Examples of suitable film formers in film coating compositions to be applied to pharmaceutical compositions of the invention comprise e.g. polyethylene glycol, polyvinylpyrrolidone, polyvinyl alcohol, hydrophilic polymers such as cationic polymers containing dimethylamino-ethyl methacrylate as functional groups (e.g. Eudragit E and EPO), hydroxypropylcellulose, hydroxymethylcellulose, and hydroxypropylmethylcellulose or the like, of which hydroxypropylmethylcellulose is preferred.

The film coating composition ingredients include plasticizers, e.g. polyethylene glycols (e.g. polyethylene glycol 6000), triethylcitrate, diethyl phthalate, propylene glycol, glycerin in conventional amounts, as well as the above-mentioned opacifiers such as titanium dioxide, and colorants, e.g. iron oxide, aluminum lakes, etc. Preferably dry mixtures as Sepifilm or Opadry mixtures, latter prepared by Colorcon Corp. are used. These products may be individually prepared dry pre-mixtures of film forming polymers, opacifiers, colorants and plasticizers which are further processed to aqueous film coating suspensions.

The film coating may be generally applied to achieve a weight increase of the tablet of about 1 to 10 wt. %, and preferably about 2 to 6 wt. %, based on the total weight of the pharmaceutical composition.

The film coating can be applied by conventional techniques in a suitable coating pan or fluidized bed apparatus using water and/or conventional organic solvents (e.g., methyl alcohol, ethyl alcohol, isopropyl alcohol), ketones (acetone), etc.

In another embodiment of the invention, the iron(III)-based phosphate adsorbent is formulated as an uniquely coated tablet.

The tablet according to the invention may be made by direct compression of the iron(III)-based phosphate (the drug substance) and by addition of high concentrations of Mg-stearate (e.g. about 3 to about 5%).

The tablet may further comprise binders as e.g. HPMC 3cPs, HP-Cellulose LH-22.

Electrostatic dry powder deposition process may increase the structural integrity of the tablet without adding major amounts of material and also provides the opportunity for an unique appearance of the dosage form.

The tablet may be coated by a electrostatic dry powder deposition process, e.g. as follows: The coating mixture is prepared by melt-extrusion of a mixture of polymer (preferably Eudragits, e.g. type E, RS. L, RL and additionally PVPNA, HPMPC, HPMCAS), coloring agent (e.g. titan dioxide) and other additives (e.g. PEG3000). A further step of micronization of the produced melt-extrudate is optionally performed, e.g. with about 7 to 10 micron.

The coating process may consist of i) fixing the core (e.g. by vacuum) on a wheel, charged, transported through the coating chamber and attaching the opposite charged coating powder to the core surface, ii) transporting the powder layered core on the wheel to an IR lamp were the coat melts, iii) transferring the core to the adjacent second wheel and repeating the process for the bottom part of the tablet core. Typical coat weights are 3-4% of the core weight and are about 20-50 μm thick.

Heat fixation step: The fusion cycle varies from product to product but typically is around 80 s per side. This includes heating up the tablets from room temperature, so the temperature at the surface of the tablet peaks at approximately 100° C. and in the tablet core approximately 70° C. for about 20 s.

According to the invention, the iron(III)-based phosphate adsorbent according to the invention may also be formulated as semi solid formulations. Such compositions are comfortable to swallow, in particular for elderly and children, and may be considered as a daily supplement rather than a medicine. Furthermore such semi-solid dosage forms have the advantage that they may be filled into multiple or single dose containers.

In one embodiment of the invention, the composition of the invention is in form of an aqueous gel formulation. Such an aqueous gel may contain a viscosity enhancer which preferably has wetting properties, or a thickener. The viscosity may be selected from polyoxyethylene sorbitan fatty acid esters, polyethylene glycols, and glycerol. The thickener may be selected from starch (e.g. corn starch, potato starch), the starch being preferably heated up, cellulose derivative (e.g. hydroxypropylmethyl cellulose), alginate salt (e.g. sodium alginate), carbomer, colloidal silicon dioxide, and other paste former (such as e.g. PVP, polyacrylic acid, arabic gum, xanthan gum and mixture thereof).

In addition, preservatives may be added, such as e.g. p-hydroxybenzoic acid methyl ester and salt thereof, p-hydroxyl benzoic acid propylester and salt thereof, sorbic acid and salt thereof, benzoic acid and salt thereof or chlorhexidine. Flavours and sweeteners may also be added. The aqueous gel may contain a buffering system, e.g. citrate or acetate buffer, to ensure the antimicrobial efficacy of the preservative system.

The aqueous gel may further contain at least one agent selected from a sweetener, such as e.g. saccharin sodium, aspartame, sucralose and a flavour, such e.g. as strawberry or passion.

The aqueous gel may be prepared by solubilizing all excipients, with the exception of the thickener in water purified, dispersing the phosphate adsorbant until vigorous mixing and then by adding the thickener.

Possible semi solid formulations include, but are not limited to, swallowable gel, e.g. aqueous or non aqueous gel (the phosphate adsorbent being optionally encapsulated or granulated); chewy bar, e.g. a cereal bar; fast-dispersing dosage, such as orally dispersing wafer; cream ball chewable dosage form; chewable dosage forms, such as candy, soft capsule, or nugget; or edible sachet. In such semi solid formulations, the iron(III)-based phosphate adsorbent may contain dietary fiber as insoluble carbohydrate, e.g. the starch may be replaced by dietary fibers.

Semi solid formulations have the advantage that they may be perceived as a daily supplement rather than a medicine, which means that a rather large dosage form may be acceptable for the patients. Preferably, these formulations are given to elderly and pediatric patients.

Swallowable gel has the advantage of be comfortable to swallow and be possibly perceived as a daily supplement rather than a medicine. In addition there is a wide choice of flavor options. Non-aqueous gels are preferred. Encapsulation of the iron hydroxide and/or a granulation step is preferably included, in order to overcome problems with mouth feeling, e.g. grittyness.

According to the invention, the chewy bar may contain ingredients selected from the groups consisting of malt extract, skimmed milk powder, fat reduced cacao, glucose syrup, egg, hardened palm oil (e.g. about 30 weight %, based on the total weight of the bar), yeast, sodium chloride (e.g. about 0.1 weight %, based on the total weight of the bar), vitamin (e.g. vitamin E), favor (e.g. vanilla flavor), one or more stabilizers (e.g. E339, E435, E472b, E475, soy bean lecithin), thickener (e.g. carob flour, E460). The bar may be covered by a milk chocolate layer, e.g. containing sugar, cacao, cacao butter, whole milk, skimmed milk powder, hazelnuts, butterfat, soy bean lecithin. The cover may weight 33% of the total weight of the chewy bar. The manufacturing process may comprise blending of all the ingredients in a mixer at elevated temperature and filling the blend into a mold. The bars may be packaged after cooling to room temperature and removal from the mold.

Chewing of a chewy bar, e.g. a cereal bar is a convenient and patient friendly administration and may be perceived as part of the daily routine, i.e. daily supplement rather than a medicine. Such a dosage form has only minor limitations with respect to the size. In addition there is a wide choice of flavor options.

Orally dispersing wafers are versatile fast-dispersing dosage form. Orally dispersing wafers containing the phosphate adsorbent of the invention, e.g. iron(III)-based phosphate are particularly suited for pediatric and geriatric populations, since they are comfortable to swallow and may be perceived as a daily supplement rather than a medicine.

According to the invention, a rapidly dispersing dosage form may release its active ingredient, i.e. the iron(III)-based phosphate adsorbent, within a period of less than about ninety seconds. These dosage forms may exhibit a three-dimensional shape, which can be retained for adequate storage but may be readily dispersed in the presence of excess moisture.

According to the invention, the rapidly dispersing dosage, e.g. the orally dispersing wafer, may be manufactured by a solid, free-form fabrication technique in which objects are built in a laminated fashion through sequential addition of patterned thin layers, e.g. three dimensional printing (3DP).

According to the invention the semi-solid dosage may be a cream ball chewable dosage form. In one embodiment of the invention, the phosphate adsorbent is suspended in a cream or gel and then layered on a core. Various flavors may be used. Such a form may provide better chewability and mouth feeling than other chewable dosage forms. This formulation may be comfortable to swallow and may be perceived as a daily supplement rather than a medicine.

According to the invention, chewable dosage forms include for example candy, soft capsule, and nugget. A wide choice of flavor may be used. Fancy shapes and colors can be designed. The chewable dosage form may be packed in a tablet dispenser or individually wrapped.

According to the invention, the chewable dosage form may contain ingredients selected from the group consisting of: corn syrup, sugar, partially hydrogenated soybean and cottonseed oil, nonfat milk powder, soy lecithin, natural or artificial flavor, citric acid, glyceryl monostearate, Carrageenan, Red 40, Vitamin (e.g. Vitamin D3 or K1), tricalcium phosphate, alpha tocopheryl, salt, niacinamide, calcium pantothenate, pyridoxine hydrochloride, riboflavin, and thiamine mononitrate.

The ingredients may be dissolved in water or in milk to form a syrup, which may be boiled until it reaches the desired concentration or the sugar starts to caramelize. The liquid may then be filled onto molds and cooled down to harden the dosage form.

According to the invention, the phosphate adsorbent, may be formulated as an edible sachet. Eating a sachet is a convenient and patient friendly administration and may be perceived as part of the daily routine, i.e. as a daily supplement rather than a medicine.

The filing of the edible sachet may be made e.g. consist of, of granules, which may be made of the material as hereinabove described for the chewy bars. For example, the filing of the edible sachet may be made by milling of the bars after removal from the mold. The sachet material may be made of water soluble polysaccharide, e.g. starch, mashed vegetable or fruits, optionally with lipids. The sachet may be manufactured by spraying the fruit or vegetable puree on a fast rotating teflonized disk where it forms a thin film which is dried in a next step.

In another embodiment of the invention, the non soluble carbohydrate contained in the iron(III)-based phosphate adsorbent is a dietary fiber, e.g. Benefiber®. For example, in step i) and/or step ii) of the manufacture process as described hereinabove, starch is replaced by dietary fiber, e.g. Benefiber®. Such a formulation combines the benefits of phosphate binding and of dietary fibers in one product.

Uses

The iron(III)-based phosphate adsorbent according to the invention exhibit valuable pharmacological properties, e.g. adsorbing inorganic phosphate or phosphate bound to foodstuffs from body fluids or foodstuffs, e.g. as indicated in in vitro and in vivo tests and are therefore indicated for therapy.

The iron(III)-based phosphate adsorbents according to the invention are, therefore, useful in the treatment and/or prevention of hyperphosphataemia, hypercalcaemia, hyperparathyroidism reduction, in cardiovascular morbidity and mortality, renal osteodystrophy, calciphylaxis and soft tissue calcifications. In particular the iron(III)-based he phosphate adsorbents according to the invention are suitable for the treatment and/or prevention of hyperphosphataemia, in humans and warm-blooded animals, in particular companion animals such as dogs and in particular cat.

The phosphate adsorbents of the invention, and pharmaceutical compositions containing them are more particularly useful in patients with hyperphosphataemia, e.g. for dialysis-dependent patients, e.g. hemodialysis, or patients suffering from advanced chronic kidney diseases (CKD), chronic renal failure, chronic renal insufficiency, end-stage renal disease.

The phosphate adsorbent according to the invention may be administered by any conventional route, in particular enterally, e.g. orally, e.g. in the form of tablets or capsules. In some cases the phosphate adsorbent may be administered through nasogastric tubes, e.g. pediatric naso-gastric tubes.

Pharmaceutical compositions comprising the compound of the invention in association with at least one pharmaceutical acceptable carrier or diluent may be manufactured in conventional manner by mixing with a pharmaceutically acceptable carrier or diluent.

Unit dosage forms for oral administration contain, for example, from about 0.5 g to about 7 g, e.g. from about 0.5 to about 5 g, e.g. from about 1.0 to about 3 g, preferably from about 1 to about 1.5, more preferably about 1 to about 1.5 g, even more preferably about 1 to about 1.25 g of phosphate adsorbent.

The phosphate adsorbent according to the invention may also be used for the absorption of phosphate bound to foodstuffs. They may be admixed with foodstuffs.

Utility of the iron(III)-based phosphate adsorbent of the invention, in the treatment of hyperphosphateamia, may be demonstrated in animal test methods as well as in clinic, for example in accordance with the methods hereinafter described.

A—Phosphate Binding capacity may be determined in assay done according to published methods, e.g. as described in WO07/088,343, the content thereof being incorporated by reference, or according to Example 3 hereinabove.

B—Clinical Trial: open label, time-lagged, multiple dose, switch study in patients with CKD (chronic kidney diseases) on hemodialysis.

Patients remain on their current sevelamer treatment during a 2-week run-in period, then enter a 1- to 2-week wash out period prior to being switched to the iron(III)-based phosphate adsorbent as described in Example 1 for 4 weeks: 3.75 g/day, 7.5 g/day, 11.25 g/day, 15 g/day, 22.5 g/day. Each cohort enrolls 10 patients. Patients are stratified by pre-study sevelamer dose: Strata 1 is less than 7.2 g/day of sevelamer in cohorts of 3.75 g/day and 7.5 g/day of the iron(III)-based phosphate adsorbent. Strata 2 is greater or equal to 7.2 g/day of sevelamer in other cohorts of the iron(III)-based phosphate adsorbent treatment.

In accordance with the foregoing the present invention provides:

1.1 An iron(III)-based phosphate adsorbent characterized by a phosphate binding capacity of at least about 120 mg adsorbed phosphate by 1 g of phosphate adsorbent, preferably of about 140 mg adsorbed phosphate by 1 g of phosphate adsorbent.

1.2 An iron(III)-based polynuclear iron(III)-based phosphate adsorbent comprising i) an adsorbent base material, preferably a non soluble carbohydrate, ii) polynuclear iron(III) oxide hydroxides, and iii) a soluble carbohydrate, e.g. glucose derivative, and iv) optionally a carbonate, wherein the soluble carbohydrate is partially incorporated into the polynuclear iron (III) oxide hydroxides.

1.3 A polynuclear iron(III)-based phosphate adsorbent comprising i) starch, ii) polynuclear iron(III) oxide hydroxides, and iii) a glucose derivative selected from sucrose, maltodextrin and mixture thereof, e.g. sucrose, wherein the glucose derivative is partially incorporated into the polynuclear iron(III) oxide hydroxides. Optionally the polynuclear iron oxide hydroxides are stabilized by said glucose derivative.

1.4 A polynuclear iron(III)-based phosphate adsorbent comprising i) a non soluble carbohydrate, e.g. starch, ii) polynuclear iron(III) oxide hydroxides, and iii) a glucose derivative selected from sucrose, maltodextrin and mixture thereof, e.g. sucrose, wherein the polynuclear iron oxide hydroxide contains polynuclear gamma-iron oxide hydroxide, and optionally ferrihydrite. Optionally the glucose derivative is partially incorporated into the polynuclear iron (III) oxide hydroxides.

1.5 An iron(III)-based phosphate adsorbent comprising an adsorbent base material, preferably a non soluble carbohydrate (e.g. starch), polynuclear iron (III) oxide hydroxides, and glucose derivative selected from sucrose, maltodextrin or mixture thereof (e.g. sucrose), wherein the polynuclear iron oxide hydroxides are stabilized by said glucose derivative.

1.6 An iron(III)-based phosphate adsorbent containing polynuclear gamma-iron oxide hydroxide and optionally ferrihydrite.

In accordance with the foregoing the present invention further provides:

2.1 A process for the preparation of an iron(III)-based phosphate adsorbent containing iron(II) oxide-hydroxide, insoluble carbohydrate (preferably starch) and a glucose derivative, which process comprises the steps of (i) reacting, e.g. simultaneously mixing, an aqueous solution of iron(III) salt with an aqueous base at pH comprised between about 6 and 10, wherein the reaction is optionally performed in the presence of said insoluble carbohydrate (preferably starch);

(ii) either adding said insoluble carbohydrate (preferably starch) if it was not present in step i)
or optionally adding more of said insoluble carbohydrate (preferably starch);

(iii) isolating the precipitate formed; and optionally washing, e.g. with water;

(iv) suspending the precipitate in an aqueous solution; and (v) adding a soluble carbohydrate (preferably a glucose derivative, such as sucrose or maltodextrin) to yield an iron(III)-based phosphate adsorbent.

2.2 A process for the preparation of an iron(III)-based phosphate adsorbent containing iron(III) oxide-hydroxide, insoluble carbohydrate (preferably starch) and a glucose derivative, which process comprises the steps of i) reacting, e.g. simultaneously mixing, an aqueous solution of iron(III) salt with an aqueous base at pH comprised between about 6 and 10, wherein the reaction is performed in the presence of said insoluble carbohydrate (preferably starch);

ii) optionally adding more of said insoluble carbohydrate (preferably starch) before the precipitation of the iron (III) is complete, e.g. has started;
wherein steps iii) to v) are performed as defined under 2.1.

2.3. A process for the preparation of an iron(III)-based phosphate adsorbent containing iron(III) oxide-hydroxide, insoluble carbohydrate (preferably starch) and a glucose derivative, which process comprises the steps of i) reacting, e.g. simultaneously mixing, an aqueous solution of iron(III) salt with an aqueous base at pH comprised between about 6 and 10;

ii) adding said insoluble carbohydrate (preferably starch), before the precipitation of the iron(III) is complete, e.g. has started;
wherein steps iii) to v) are performed as defined under 2.1.

2.4 A process for the preparation of an iron(III)-based phosphate adsorbent containing iron(III) oxide-hydroxide, starch and a glucose derivative, which process comprises the steps of i) reacting, e.g. simultaneously mixing, an aqueous solution of iron(III) salt with an aqueous base, and ii) either performing step i) in presence of an insoluble carbohydrate, e.g. starch, and optionally adding more insoluble carbohydrate after the complete mixing:
or adding the insoluble carbohydrate after the reaction of step i), e.g. after the complete mixing,
wherein steps iii) to v) are performed as defined under 2.1.

2.5. A process for the preparation of an iron(III)-based phosphate adsorbent containing iron(III) oxide-hydroxide, insoluble carbohydrate (preferably starch) and a glucose derivative, which process comprises the steps of i) reacting, e.g. simultaneously mixing, an aqueous solution of iron(III) salt with an aqueous base, in presence of an insoluble carbohydrate (preferably starch), wherein the pH of the solution is maintained at a value between about 6 and 8;
wherein steps iii) to v) are performed as defined under 2.1.

2.6. A process as defined under 2.1 to 2.5 wherein the process further comprises the step vi) of isolating the product, preferably by spray drying or fluidized spray drying to give an iron(III)-based phosphate adsorbent as a dry powder.

2.7. A process as defined under 2.1 to 2.6 wherein the process further comprises the step of granulating the powder, optionally in presence of at least one excipient selected from a binder and a lubricant, to yield an iron(III)-based phosphate adsorbent as a granulate.
2.8. A process as defined under 2.1 to 2.7 wherein the process further comprises the step viii) of tabletting either the powder obtained in step vi) or the granulate obtained in step vii), wherein the tabletting step is optionally performed in presence of an excipient selected from a filler, a binder, a disintegrant, a flow agent, a lubricant, and mixture thereof, as hereinabove described.

Furthermore according to the invention there is provided:
3. A process for the preparation of gamma-iron(III) oxide-hydroxide, which process comprises the steps of
   a) reacting an aqueous solution of iron(III) salt (e.g. iron (III) chloride) with a aqueous base at pH comprised between 6 and 10, wherein the reaction is optionally performed in the presence of starch;
   b) adding starch if starch was not present in step a), and optionally
   a) isolating the solids and washing.

In accordance with the foregoing the present invention further provides:
4.1 A method for preventing or treating disorders or diseases such as indicated above, in a subject in need of such treatment, i.e. a human or a warm-blooded animal, in particular companion animal such as dog and cat, which method comprises administering to said subject an effective amount of an iron(III)-based phosphate adsorbent according to the invention.
4.2 A method for controlling serum phosphate and serum calcium-phosphate product levels, while maintaining normal serum calcium levels, in a subject in need of such treatment, e.g. in patients on chronic hemodialysis, which method comprises administering to said subject an effective amount of an iron(III)-based phosphate adsorbent according to the invention.
4.3 A method for selectively removing inorganic phosphate or eliminating inorganic phosphate, e.g. from dialysis fluids, whole blood, plasma, in a subject in need of such treatment, e.g. in patients on dialysis, e.g. on chronic hemodialysis, which method comprises administering to said subject an effective amount of an iron(III)-based phosphate adsorbent according to the invention.
4.4 A method for selectively removing inorganic phosphate bound to foodstuffs.
5.1 A phosphate adsorbent according to the invention for use as a pharmaceutical, e.g. in any of the methods as indicated under 4.1 to 4.3 above.
6. Composition for use as a pharmaceutical preparation for the selective elimination of inorganic phosphate from liquids, wherein the composition is insoluble in water and contains an iron(III)-based phosphate adsorbent as defined in any preceding claims
7.1 A pharmaceutical composition, e.g. for use in any of the methods as in 4.1 to 4.3 above comprising an iron(III)-based phosphate adsorbent according to the invention in association with a pharmaceutically acceptable diluent or carrier therefore, e.g. comprising at least one excipient selected from a preservative and a binder.
7.2 A pharmaceutical composition, e.g. for use as a pharmaceutical preparation for the selective elimination of inorganic phosphate from liquids, e.g. dialysis fluids, whole blood or plasma, wherein the composition contains an iron(III)-based phosphate adsorbent material according to the invention.
7.3 A pharmaceutical composition suitable for oral administration, e.g. a solid or semi solid dosage form, containing the iron(III)-based phosphate adsorbent according to the invention.
7.4 A solid or semi solid dosage form containing the iron(III)-based phosphate adsorbent according to the invention.
7.5 Pharmaceutical composition, preferably a powder or a granulate, comprising the iron(III)-based phosphate adsorbent according to the invention and further comprising a preservative (e.g. an alcohol, preferably ethanol) and optionally a binder (e.g. sucrose, microcrystalline cellulose or mixture thereof).
7.6 Pharmaceutical composition according to the invention which is in form of a tablet and further comprises a lubricant, and optionally at least one further excipient selected from a filler, a binder, a disintegrant, and a flow agent.
8. An iron(III)-based phosphate adsorbent according to the invention for use in the preparation of a pharmaceutical composition for use in any of the method as in 4.1 to 4.3 above.

According to the invention, the phosphate adsorbent may be administered as the sole active ingredient or together with another phosphate reducing agent, such as sevelamer; Fosrenol; Ca acetate; or Ca carbonate. It may also be administered in combination with a calcimimetic such as cinacalcet; vitamin D; or calcitriol.

In accordance with the foregoing the present invention provides in a yet further aspect:
9. A method as defined above comprising co-administration, e.g. concomitantly or in sequence, of a therapeutically effective amount of a phosphate adsorbent according to the invention, and a second drug substance, said second drug substance being another Phosphate reducing agent, a calcimimetic, vitamin D, or calcitriol, e.g. as indicated above.
10. A therapeutic combination, e.g. a kit, comprising a) a phosphate adsorbent according to the invention, and b) at least one second agent selected from an another Phosphate reducing agent, a calcimimetic, vitamin D and calcitriol. Component a) and component b) may be used concomitantly or in sequence. The kit may comprise instructions for its administration.

Where a phosphate adsorbent according to the invention is administered in conjunction with another phosphate reducing agent, such as sevelamer, Fosrenol, Ca acetate or Ca carbonate; a calcimimetic such as cinacalcet; or with vitamin D or calcitriol, e.g. for preventing or treating hyperphosphataemia or other diseases or disorders as hereinabove specified, dosages of the co-administered compound will of course vary depending on the type of co-drug employed, on the condition being treated and so forth.

EXAMPLES

The following examples are illustrative of the invention.

Example 1

Preparation of Iron(III)-Based Phosphate Adsorbent

To a mixture of 41 kg potato starch, 118 kg sodium carbonate and 480 kg water a solution of 148 kg iron(III) chloride hexahydrate dissolved in 588 kg water is added over 30 minutes time span at a temperature of 20-35° C. The resulting brown suspension is stirred for at least 60 minutes at 25° C. then filtered and washed three times with 968 kg water each using a decanter centrifuge. Subsequent 160 kg water, 41 kg sucrose and 129 kg ethanol are added and the mixture is stirred for at least 60 minutes. 172 kg of the final product are isolated as a reddish brown powder, obtained by spray drying using a NIRO SD42 with appropriate spray drying parameters or with an atomization pressure of 1.2 bar, an outlet temperature of 65° C. and an Inlet temperature of 140° C.

The product may be filled without any other processing directly into sachets or stick packs.

Example 2

Preparation of Iron(III)-Based Phosphate Adsorbent

An aqueous solution of 21.1 g sodium carbonate dissolved in 105 g water (solution A) and an aqueous solution of 26.5 g iron(III) chloride hexahydrate dissolved in 55 g water (solution B) are prepared. Solution A (4.2 g/min) and B (2.7 g/min) are dosed to a suspension of 7.36 g potato starch in 40 g water over a time span of 30 minutes by continuous mixing of solution A and B and subsequent addition to the potato starch suspension. The resulting brown-reddish suspension is stirred for at least one hour at 25° C., filtered and washed three times with 173.6 g water each. To the resulting reddish brown solids 14.6 g water, 7.36 g sucrose and 24.2 g ethanol are added and the mixture is stirred for 60 minutes. 18.4 g of the final product are obtained by fluidized spray drying using appropriate FSD conditions.

Example 3

Phosphate Binding Capacity of the Material Described in Example 1 or Example 2 Determined by Ion Chromatography/Conductivity Detection Separation mechanism used is ion exchange.

Reagents: Highly pure water (e.g. from Milli-Q-System (Millipore)); Sodium hydroxide (50% (m/m) solution, carbonate free, e.g. Merck 1.58793); 0.1 N Hydrochloric acid (HCl); Hydrochloric acid 37%; Sodium hydrogen phosphate ($Na_2HPO4$).

Equipment: Ion chromatograph with gradient pump; Anion exchange column (e.g. Dionex IonPac AS11-HC Length 250 mm, internal diameter 4 mm; or equivalent); Self regenerating anion suppressor (e.g. Dionex ASRS-ULTRA II 4 mm, anion suppressor system), PVDF Filter (e.g. Infochroma: 8817E-PV-4 ECO HPLC-Filter PVDF 0.45 μm).

Chromatographic Conditions

Gradient elution using degassed water as eluent 1 and 80 mM sodium hydroxide in water as eluent 2.

|  | Time | OH⁻ [mM] | % E1 | % E2 | Remark |
|---|---|---|---|---|---|
| Gradient program | 0 | 16 | 80 | 20 | Run start |
|  | 10 | 80 | 0 | 100 |  |
|  | 14 | 80 | 0 | 100 |  |
|  | 14.1 | 16 | 80 | 20 |  |
|  | 16.0 | 16 | 80 | 20 | Run end |
|  | 18.0 | 16 | 80 | 20 |  |
| Flow rate | 0.6 mL/min |  |  |  |  |
| Detection | Suppressed electrical conductivity |  |  |  |  |
| Column temperature | 30° C. |  |  |  |  |
| Injection volume | 25 μL |  |  |  |  |

System Suitability Test (SST)

The system suitability test proves that chloride and phosphate are sufficiently separated. Moreover the repeatability of injection is shown by repetitive injection of the comparison solution for calculation. A blank chromatogram shows that no interfering peak exist in the solvent. A 1/100 dilution of the comparison solution for calculation is used to show sensitivity of the system.

Preparation of Solutions

| | |
|---|---|
| Test solution (prepare in duplicate TSx.1 and TSx.2) | Accurately weigh (to within 0.01 mg) 365.0 to 385.0 mg of the test substance into a 25 mL volumetric flask. Add 20.0 mL of CS1 to this substance and let stand for 10 min. Adjust the pH of this suspension to pH 2.0 with HCl 0.1N and fill to the mark with water. The tightly closed flask is then kept in a water bath of 37° C. for 2 hours. Approximately, every half an hour the suspension is stirred manually by shaking the vial. Afterwards, filter approximately 2.0 mL of the resulting suspension through a 0.45 μm filter (PVDF) into a vial. Take 1.0 mL of this filtrate into a 25 mL volumetric flask and fill to the mark with water. The clear and colorless solution will be used directly for chromatography. |
| Comparison stock solution (prepare single: CS1) | Concentration ($PO_4^{3-}$) level for CS1 = 4273 μg/mL Preparation: Accurately weigh (to within 0.1 mg) 6350 mg to 6425 mg of $Na_2HPO_4$ into a 1000 mL volumetric flask, dissolve with app. 900 mL water and set to pH 2.0 with HCl 37% and 0.1N. Then fill to the mark with solvent. |
| Comparison solution for calculation (prepare single: CS2) | Concentration ($PO_4^{3-}$) level for CS2 = 170.9 μg/mL Preparation: Pipette 2.0 mL of CS1 into a 50 mL volumetric flask and fill to the mark with solvent. |

Evaluation/Assessment

The analyte peaks in the chromatograms of the test solution is identified by comparing the retention times with those of the peaks in the chromatograms of the comparison solutions.

The peak areas for each analyte peak is determined in the chromatograms of the test solutions. The peak areas for each analyte peak is also determined in the chromatograms of the CS2 solutions.

Calculation

Percent Adsorption (%) (m/m) of Phosphate $$1.\ ABS_{PO_4}(\%;\ m/m) = \frac{m_{PO_4\ added} - m_{PO_4\ measured}}{EW_{TS}} \times 100\ \%$$

-continued $$2.\ m_{PO_4\ added}\ [mg] = EW_{Na_2HPO_4} \times \frac{MW_{PO_4^{3-}}}{MW_{Na_2HPO_4}} \times \frac{1}{50}$$

$$3.\ m_{PO_4\ measured}\ [mg] = EW_{Na_2HPO_4} \times \frac{MW_{PO_4^{3-}}}{MW_{Na_2HPO_4}} \times \frac{1}{40} \times \frac{PA_{TS}}{PA_{CS2}}$$

$EW_{TS}$ Weight of the material described in Example 1 or Example 2 in test solution [mg]
$EW_{Na2HPO4}$ Weight of sodium hydrogen phosphate in CS1 solution [mg]
$PA_{TS}$ Peak area of phosphate in test solution
$PA_{CS2}$ Peak area of phosphate in comparison solution 2
$MW_{PO4}{}^{3-}$ Molecular weight of phosphate: 94.97 g/mol
$MW_{Na2HPO4}$ Molecular weight of sodium hydrogen phosphate: 141.96 g/mol Results:

The compound of example 1 adsorbs 14.2% m/m phosphate.

The compound of example 2 adsorbs 20% m/m phosphate.

Example 4

Sachet

90% of the product as prepared in example 1 is mixed together with corn starch (10%) to prepare the final blend. The final blend is then filled into sachets.

Example 5

Capsules (Direct Fill with Lubricant)

90% of the product as prepared in example 1 is filled into a mixer. A pre-mix of 7-8% of the same product and 2-3% Mg-stearate is prepared. The premix is screened through a screen (1000 micron mesh size) into the mixer with the rest of the product to prepare the final blend. The final blend is then filled into hard gelatin capsules.

Example 6

Capsules (Direct Fill with Lubricant and Additional Excipient)

80% of the product as prepared in example 1 is mixed together with MCC (10%) or preferably corn starch (10%). A pre-mix of 7-8% of the same product and 2-3% Mg-stearate is prepared. The premix is screened through a screen (1000 micron mesh size) into the mixer with the rest of the product to prepare the final blend. The final blend is then filled into hard gelatin capsules.

Example 7

Sachet, Stick Pack or Capsule (Granulation by Dry Compaction)

68% of the product as prepared in example 1 is mixed together with MCC (20-30%). Mg-stearate (2%) is screened (1000 micron mesh size) and added to this pre-mixture. The final blend is prepared, and then compacted and/or compressed. The compaction is made with a tabletting machine with big punches or a roller compaction machine Then the comprimates are milled through a screen, mesh size 2 mm. Subsequently, the screened granulate is filled into sachets or stickpacks.

The granulate could also be filled together with a lubricant into capsules.

Example 8

Sachet, Stick Pack or Capsule (Wet Granulation)

The product as prepared in example 1 is granulated with about 15% water, related to the dry powder in a high shear mixer. Then the granulate is dried until a LOD (loss on drying) of approx. 6-7% is reached. Then the dried granulate is screened through a screen, mesh size 2 mm. Finally the screened granulate is filled into stick packs. Optionally, the granulate may also be filled together with a lubricant into capsules.

Example 9

Sachet, Stick Pack or Capsule (By Wet Granulation with Additional Binder)

About 97% of the product as prepared in example 1 is mixed with about 2% hydroxyproyl methylcellulose-HPMC-3 cps, grade 2910 as binder, and granulated with approximately 10% water, related to the dry powder. The binder is added as solution after dissolving in the corresponding amount of water. The subsequent steps are as described in the example above.

Example 10

Tablet (Direct Compression with Lubricant)

90% of the product as prepared in example 1 is filled into a mixer. A pre-mix of 7% of the same product and 3% Mg-stearate is prepared. The premix is screened through a screen (1000 micron mesh size) into the mixer with the rest of the product to prepare the final blend. The final blend is then compressed on a tabletting machine to tablets of 644 mg weight (corresponds to 625 mg of product 1).

Example 11

Tablet (Direct Compression with Lubricant and Additional Excipients)

50% of the product as prepared in example 1 is filled into a mixer together with 30% microcrystalline cellulose and about 10% crospovidone. A pre-mix of approx. 7% of the same product and 3% Mg-stearate is prepared. The premix is screened through a screen (1000 micron mesh size) into the mixer with the rest of the product to prepare the final blend. The final blend is then compressed on a tabletting machine to ovaloid tablets of 1100 mg weight (corresponds to 625 mg of product). The tablets are coated with an aqueous suspension of film forming polymer (HPMC 3 cps), coloring agent(s), titanium dioxide (white pigment), talk (glidant) and plasticizer(s).

Example 12

Tablet (Granulation by Dry Compaction)

Proceed as described in example 7 but disintegrant is additionally contained in the granulate. Also, an external phase comprising a filler, disintegrant, glidant and lubricant is added to the screened granulate and the final blend is then compressed to tablets which may subsequently be coated.

Example 13

Tablet (by Wet Granulation with Additional Binder and Other Excipients)

50% of the product as prepared in example 1 is granulated together with approx. 20% microcrystalline cellulose and approx. 5% crospovidone, with approximately 18% water, related to the dry powder, in a high shear mixer. Then the granulate is dried until a LOD (loss on drying) of about 6-7% is reached. Then the dried granulate is screened through a screen, mesh size approx. 1.25 mm into a mixer together with 10% microcrystalline cellulose and approx. 5% crospovidone. A pre-mix of approx. 7% of this mix and about 2% Mg-stearate is prepared. The premix is screened through a screen (1000 micron mesh size) into the mixer with the rest of the product to prepare the final blend. The final blend is then compressed on a tabletting machine to ovaloid tablets of 1100 mg weight (corresponds to 625 mg of product). The tablets are coated with an aqueous suspension of HPMC 3 cps, titanium dioxide, talk and plasticizer(s) or of the corresponding Opadry mixture.

Example 14

Tablet (Wet Granulation with Additional Binder)

As describe above but with the addition of about 3% hydroxyproyl methylcellulose-HPMC-3 cps, grade 2910 in the inner phase whereby the binder is added in the dry state or partially or entirely dissolved in the granulation liquid; the amount of binder is compensated by the amount of filler in the granulate. The subsequent steps are as described in the example above.

Example 14

Gel (Plain aqueous gel) 80 mL of water is heated up to about 70°-75° C. 20 g of the product as prepared in example 2 is added and the suspension is kept at 70° C. until a jelly mass is being formed. The gel is maintained at 70° C. for some minutes to stabilize the gel forming process. After cooling to room temperature, water is added to compensate for potential losses of evaporated water during manufacture.

Example 15

Gel 1.5 mg/mL of benzoate sodium is dissolved in water purified, add 0.2 mg/mL of saccharin sodium, 1.0 mg/mL of strawberry flavor and the citrate buffering system. After complete dissolution, 5 mg/mL of polysorbate 20 is added, then the phosphate adsorbent is dispersed under mixing. A homogeneous suspension is formed. Finally, 30 mg/mL of hydroxypropylmethyl cellulose is slowly added under mixing.

Examples 16-20

The following ingredients (in mg) are dissolved or suspended in glycerol, mixed together and filled-into stick pack.

|  | Ex 16 | Ex 17 | Ex 18 | Ex 19 | Ex 20 |
| --- | --- | --- | --- | --- | --- |
| Phosphate adsorbent of example 2 | 800 | 800 | 800 | 800 | 800 |
| HPMC | 50 | / | 50 | 50 | 50 |
| Gum arabicum | 50 | / | 50 | 50 | 50 |
| Palatone | 20 | / | 20 | 20 | 20 |
| Simethicone | 20 | / | 20 | 20 | 20 |
| Silicium dioxide | / | 50 | / | / | / |
| Hydroxyl ethyl cellulose | / | 100 | / | / | / |
| Sodium cyclamate | 5 | 5 | 5 | 5 | 5 |
| Methyl-4-hydroxy-benzoate | 10 | 10 | 10 | 10 | 10 |
| Propyl-4-hydroxy-benzoate | 5 | 5 | 5 | 5 | 5 |
| Caramel flavor | 1 | 1 | 1 | 1 | 1 |
| Ethanol | Ad. 10 ml | Ad. 10 ml |  |  |  |
| Proylene glycol |  |  | Ad. 10 ml |  |  |
| Glycerol |  |  |  | Ad. 10 ml |  |
| Corn oil |  |  |  |  | Ad. 10 ml |

Examples 21-22

Oral Dispersing Wafer

The following ingredients (mg) are mixed together.

|  | Ex 21 | Ex 22 |
| --- | --- | --- |
| Phosphate adsorbent of example 2 | 400 | 400 |
| Lactose monohydrate | 472 | 472 |
| Microcrystalline cellulose | 140 | 140 |
| Starch | 70 | / |
| Arabinogalactan | / | 70 |

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The invention claimed is:

1. A process for preparing an iron(III)-based phosphate adsorbent comprising iron(III) oxide-hydroxide, starch and sucrose, said process comprising:
   (i) reacting an aqueous solution of iron(III) salt with an aqueous base at a pH from between 6 and 10 to form a mixture in which an iron oxide hydroxide precipitate begins to form;
   (ii) adding starch to the mixture of step i) prior to complete formation of the iron oxide hydroxide precipitate;

(iii) allowing complete formation of the iron oxide hydroxide precipitate to occur;
(iv) isolating the precipitate formed according to step (iii);
(v) suspending the isolated precipitate from step (iv) in an aqueous solution;
(vi) adding sucrose and optionally at least one excipient selected from a preservative and a binder; and
(vii) fluidized spray drying the solution from step to (vi) to yield an iron(III)-based phosphate adsorbent as a dry powder.

2. The process according to claim 1, wherein at least one washing is performed between step (iv) and (v).

3. The process according to 2, wherein in step (i) the pH of the solution is maintained at a constant value between 6 and 8.

4. The process according to claim 2, further comprising the step (viii) of granulating the dry powder in the presence of an excipient selected from a binder and a lubricant to yield an iron(III)-based phosphate adsorbent as a granulate.

5. The process according to claim 4, wherein the process further comprises the step (ix) of tableting the granulate in the presence of an excipient selected from the group consisting of a filler, a binder, a disintegrant, a flow agent, a lubricant, and mixtures thereof.

6. The process according to claim 1, wherein the iron(III)-based phosphate adsorbent comprises starch in an amount of about 10% to about 35% by weight.

7. The process according to claim 6, wherein the iron(III)-based phosphate adsorbent comprises sucrose in an amount of about 5% to about 50% by weight.

8. The process according to claim 6, wherein the iron(III)-based phosphate adsorbent comprises iron in an amount of at least 10% by weight.

9. The process according to claim 1, wherein the aqueous base is sodium carbonate.

* * * * *